(12) United States Patent
Ma et al.

(10) Patent No.: US 9,610,133 B2
(45) Date of Patent: Apr. 4, 2017

(54) WIRELESS LAPAROSCOPIC CAMERA

(75) Inventors: Yong Ma, Cheshire, CT (US); Eric Stanley, Milford, CT (US); Ravi Durvasula, Cheshire, CT (US); James Power, Madison, CT (US)

(73) Assignee: Covidien LP, Mansfield, MA (US)

(*) Notice: Subject to any disclaimer, the term of this patent is extended or adjusted under 35 U.S.C. 154(b) by 641 days.

(21) Appl. No.: 13/025,636

(22) Filed: Feb. 14, 2011

(65) Prior Publication Data

US 2011/0261183 A1    Oct. 27, 2011

Related U.S. Application Data

(60) Provisional application No. 61/314,186, filed on Mar. 16, 2010.

(51) Int. Cl.
*A61B 90/00* (2016.01)
*A61B 1/05* (2006.01)
*A61B 17/00* (2006.01)

(52) U.S. Cl.
CPC ........... *A61B 90/361* (2016.02); *A61B 1/051* (2013.01); *A61B 2017/00221* (2013.01); *A61B 2017/00734* (2013.01)

(58) Field of Classification Search
USPC .......................................................... 348/77
See application file for complete search history.

(56) References Cited

U.S. PATENT DOCUMENTS

| 5,494,483 A | 2/1996 | Adair | |
|---|---|---|---|
| 5,879,289 A * | 3/1999 | Yarush et al. | 600/179 |
| 7,194,917 B2 | 3/2007 | Dung | |
| 7,570,295 B2 | 8/2009 | Funato et al. | |
| 7,927,272 B2 | 4/2011 | Bayer et al. | |
| 7,999,845 B2 * | 8/2011 | Abe | 348/74 |
| 2002/0067408 A1 * | 6/2002 | Adair et al. | 348/76 |
| 2003/0220542 A1 | 11/2003 | Belson et al. | |
| 2007/0070195 A1 * | 3/2007 | Abe | 348/74 |
| 2008/0033450 A1 | 2/2008 | Bayer et al. | |
| 2008/0309758 A1 * | 12/2008 | Karasawa et al. | 348/65 |
| 2008/0312500 A1 | 12/2008 | Asada et al. | |
| 2009/0051763 A1 * | 2/2009 | Adler et al. | 348/65 |
| 2009/0054787 A1 | 2/2009 | Adler et al. | |
| 2009/0147076 A1 * | 6/2009 | Ertas | 348/65 |
| 2010/0244217 A1 * | 9/2010 | Ha et al. | 257/686 |

FOREIGN PATENT DOCUMENTS

WO    2009063224 A2    5/2009

OTHER PUBLICATIONS

European Search Report 11250310.7-1269 dated Jun. 2, 2011.

* cited by examiner

*Primary Examiner* — Dave Czekaj
*Assistant Examiner* — Kehinde O Abimbola

(57) ABSTRACT

A wireless laparoscopic camera system includes a housing having proximal and distal ends and a lens disposed at the distal end thereof. A chip package is disposed within the housing. The chip package is positioned proximally of the lens and includes an image sensor, a processing component, and a wireless transmitter. The image sensor, the processing component, and the wireless transmitter are configured as bare die and are stacked and coupled in sequence with respect to one another to form the chip package. The chip package is configured to convert an optical image produced by the lens into an electrical signal. The signal is transmitted wirelessly to a wireless receiver positioned remote of the housing.

14 Claims, 2 Drawing Sheets

WIRELESS LAPAROSCOPIC CAMERA

CROSS REFERENCE TO RELATED APPLICATION

The present application claims the benefit of and priority to U.S. Provisional Application Ser. No. 61/314,186 filed on Mar. 16, 2010, the entire contents of which are incorporated herein by reference.

BACKGROUND

Technical Field

The present disclosure relates to a laparoscopic camera, and more particularly, to a wireless video camera and system for use in laparoscopic surgeries.

Background of Related Art

Due to recent advancements in minimally invasive, or laparoscopic surgical technology, the number of surgeries capable of being performed laparoscopicly has greatly increased. Laparoscopic surgical procedures are minimally invasive procedures in which operations are carried out within the body by means of elongated instruments inserted through small incisions in the body. The incisions are typically created by a tissue piercing instrument such as a trocar. Laparoscopic instruments are inserted into the patient through a cannula or port which maintains the incision opening in the body during the procedure.

Laparoscopic procedures are desirable in that they allow for quicker recovery time and shorter hospital stays as compared to open surgical procedures. Laparoscopic procedures also leave minimal scarring (both internally and externally) and reduce patient discomfort during the recovery period.

However, because the interior dimensions of the cannulas and/or access ports used in laparoscopic procedures are necessarily small, only elongated, small diametered instrumentation may be used to access the internal body cavities and organs. Visibility into the surgical site is also limited, if not completely occluded.

Accordingly, it would be desirable to provide a wireless laparoscopic camera configured for insertion through relatively small cannulas and/or access ports and into an internal body cavity which is capable of providing the surgeon with a real-time video image of the surgical site.

SUMMARY

In accordance with the present disclosure, a wireless laparoscopic camera system is provided. The wireless laparoscopic camera system includes a housing having a proximal end and a distal end. The housing is configured for insertion into an internal body cavity. A lens is disposed at the distal end of the housing. A chip package is disposed within the housing and is positioned proximally of the lens. The chip package includes an image sensor, a processing component, and a wireless transmitter. The image sensor, the processing component, and the wireless transmitter are configured as bare die, or integrated circuits, and are stacked and coupled in sequence with respect to one another to form the chip package. The chip package is configured to convert an optical image produced by the lens into an electrical signal. The electrical signal is then transmitted wirelessly to a wireless receiver positioned remote of the housing.

In one embodiment, an antenna is disposed at the proximal end of the housing. The antenna is configured to facilitate the wireless transmission of the signal to the wireless receiver.

In another embodiment, the wireless receiver is coupled to a video display for displaying the transmitted signal as a video image.

In still yet another embodiment, the laparoscopic camera includes one or more batteries disposed within the housing for powering the chip package. The housing may also include a battery charging circuit disposed therein. The battery charging circuit is configured for charging the at least one battery. A power transmitter positioned remote of the housing may be provided for wirelessly transmitting power, e.g., by radio frequency (RF) power transfer, to the battery charging circuit.

In another embodiment, the housing includes a clip disposed on an outer surface thereof. The clip is configured to releasably engage the housing to a shaft or other portion of a surgical instrument.

BRIEF DESCRIPTION OF THE DRAWINGS

Various embodiments of the present disclosure are described herein with reference to the drawings wherein.

DETAILED DESCRIPTION

Figure 1:
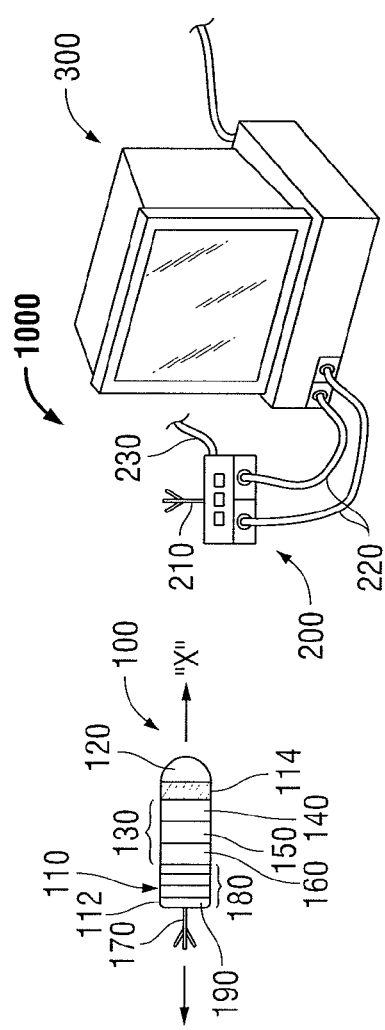
FIG. 1 is a schematic of a wireless laparoscopic camera system in accordance with the present disclosure.

Turning now to FIG. 1, a wireless laparoscopic camera system in accordance with the present disclosure is shown indicated by reference numeral 1000. Wireless laparoscopic camera system 1000 generally includes a wireless camera 100, a remote receiver, or transceiver 200 and a video display 300. As will be described in greater detail hereinbelow, wireless camera 100 includes a housing 110 configured to house the various components of wireless camera 100. An antenna 170 extends from a proximal end 112 of housing 110. Alternatively, antenna 170 may be internally disposed within housing 110. Antenna 170 is configured to facilitate wireless communication between the wireless camera 100 and the remote receiver, or transceiver 200. Remote receiver 200 likewise includes an antenna 210 to facilitate wireless communication therebetween. Cables 220 couple remote receiver 200 to video display 300. Further, remote receiver 200 is adapted to connect to an energy source (not shown) via cable 230.

Housing 110 of wireless camera 100 is generally cylindrical in shape and defines a longitudinal axis "X." It is envisioned that housing 110 define a relatively low profile configuration such that wireless camera 100, when disposed on a laparoscopic instrument, e.g., surgical instrument 400 (FIG. 2), does not inhibit surgical instrument 400 (FIG. 2) from being inserted through a relatively small incision in tissue, or access port (not shown), as is often required during laparoscopic procedures. It is also envisioned that housing 110 be formed from, or coated with a biocompatible material such that wireless camera 100 may be inserted into an internal body cavity without the risk of an allergic reaction or rejection by surrounding tissue. Additionally, housing 110 may define a relatively smooth surface geometry so as to prevent wireless camera 100 from catching on tissue or tearing tissue during insertion, use and/or removal of the wireless laparoscopic camera 100 from an internal body cavity. Further, wireless camera 100 may be configured to clip-on or otherwise engage a surgical instrument, e.g., surgical forceps 400 (FIG. 2), or, alternatively, may simply be positioned within the internal body cavity. In either embodiment, wireless camera 100 is configured to wirelessly communicate with a remote wireless receiver 200 positioned externally of the body to provide a real-time video image of the surgical site.

With continued reference to FIG. 1, the components of wireless laparoscopic camera 100 will now be described in detail. Disposed at a distal end 114 of housing 110 is an optical lens 120 (or series of lenses). The lens 120 is configured to project an optical image onto an image sensor 140 that is disposed within the housing 110 and positioned proximal of the lens 120. The image sensor 140 is manufactured as a bare die, or integrated circuit and is packaged together with a bare die processing component 150 and a bare die wireless transmitter, or transceiver 160. The image sensor 140, processing component 150, and wireless transmitter 160 are disposed within housing 110 and are stacked and coupled in sequence distally to proximally from the lens 120 in a single "chip-stack" package 130. Stacking the relatively thin bare die image sensor 140, bare die processing component 150, and bare die wireless transmitter 160 in a single package 130 allows the package 130 to operate as a single "chip" having a reduced area. As can be appreciated, such a configuration reduces the overall size, and, more particularly, the diameter of the housing 110, as is desired for laparoscopic instruments.

Positioned proximally of the chip package 130 and coupled thereto is one or more batteries 180 configured to power the chip package 130. The batteries 180 are generally disc-shaped and are stacked within the housing 110. As can be appreciated, the lens 120, chip package 130 (which includes the image sensor 140, the processing component 150, and the wireless transmitter 160) and the batteries 180 are all stacked in columnar fashion about longitudinal axis "X" and are disposed within the relatively small diametered cylindrical housing 110 of wireless laparoscopic camera 100.

With continued reference to FIG. 1, an antenna 170 is disposed at the proximal end 112 of housing 110 and extends proximally and axially from the housing 110 along longitudinal axis "X." The antenna 170 is configured to facilitate wireless communication between the wireless camera 100 and the wireless receiver 200. A battery charging circuit 190 may also be disposed within the housing 110. The battery charging circuit 190 is positioned in column with and proximally of the batteries 180 and is configured to charge the batteries 180, as will be described in greater detail below.

As mentioned above, a wireless receiver, or transceiver 200 is positioned remove of the wireless camera 100 and is configured to wirelessly communicate with the wireless camera 100. More particularly, the receiver 200 receives an electrical signal from the wireless camera 100, decouples the signal and feeds the signal, e.g., via cables 220, to a video monitor 300 to display the signal as a video image. The receiver 200 may include an antenna 210 to facilitate wireless communication between the wireless camera 100 and the receiver 200. Further, the receiver 200 may be configured as a transceiver 200, functioning to both receive the signal from the wireless camera 100 and to transfer energy to the battery charging circuit 190 to charge the batteries 180, as will be described in greater detail below.

Figure 2:
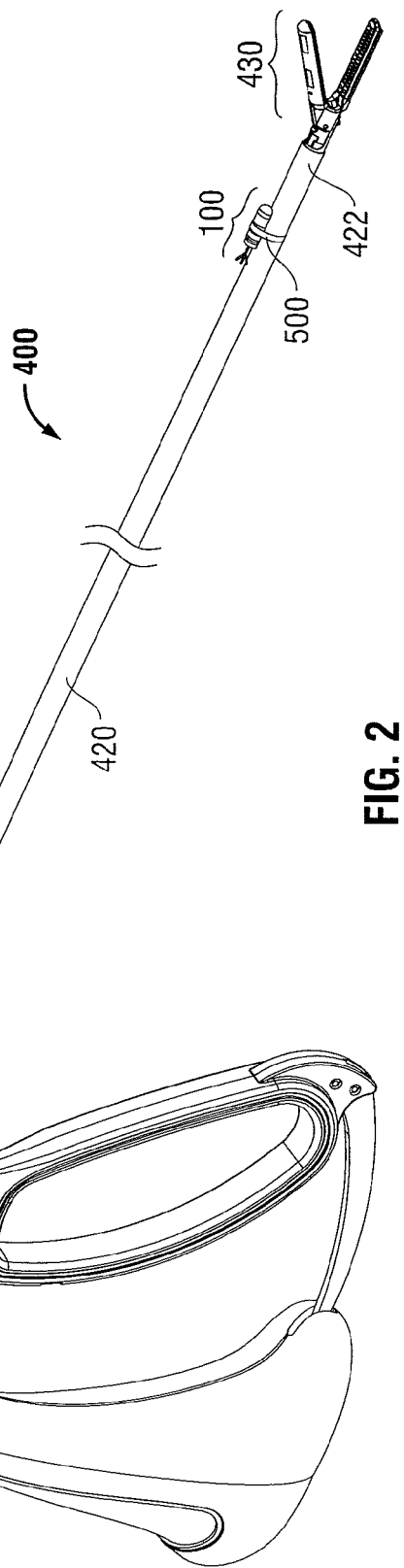
FIG. 2 is a perspective view of a surgical instrument having a wireless laparoscopic camera mounted thereto.
Figure 3:
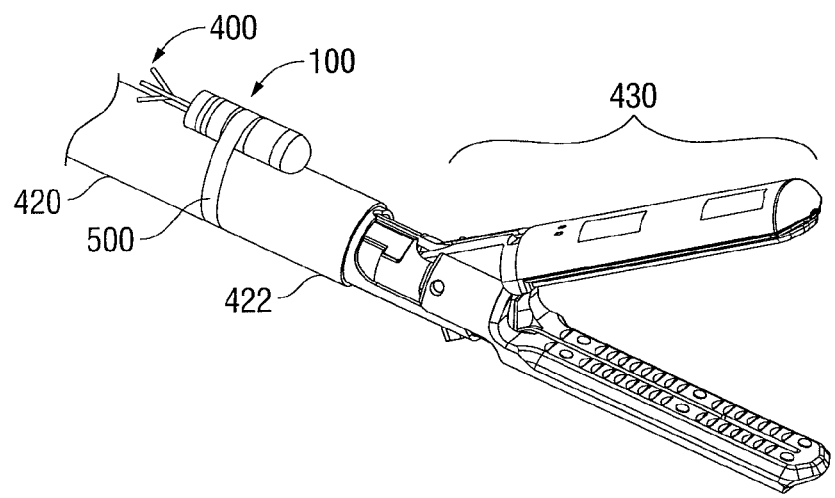
FIG. 3 is an enlarged, perspective view of a distal end of the surgical instrument of FIG. 2 shown having the wireless laparoscopic camera mounted thereto.

Referring now to FIGS. 2-3, a surgical instrument 400, and more particularly, a surgical forceps 400, is shown generally including a handle 410, an elongated shaft 420 and an end effector 430 disposed at a distal end of the elongated shaft 420. Wireless laparoscopic camera 100 is disposed, e.g., clipped or mounted, onto elongated shaft 420 toward the distal end 422 thereof. Although surgical instrument 400 is shown as a surgical forceps 400, it is envisioned that wireless camera 100 may be clipped, or mounted onto various other surgical instruments. Further, clip 500 may be configured to engage camera 100 to surgical instrument 400 at various positions along shaft 420 or on end effector 430, depending, for example, on the dimensions of the surgical instrument, the particular procedure to be performed, and/or the desired field of view. However, as mentioned above, camera 100 need not be engaged to a surgical instrument, but may simply be positioned within the internal body for providing a video image of the surgical site.

The operation of wireless laparoscopic camera 100 and corresponding wireless camera system 1000 will now be described with reference to FIG. 4. As mentioned above, optical lens 120 projects (1) an optical image of the field of view, e.g., the surgical site, onto the image sensor 140. The image sensor 140, which is coupled to the processing component 150 and wireless transmitter 160 within chip package 130, converts the optical image into an electrical signal and communicates (2) the electrical signal to the processing component 150. The processing component 150 may be configured to convert the signal from an analog signal to a digital signal, from a digital signal to an analog signal, or to modulate the signal. The processed signal is then communicated (3) to the wireless transmitter 160. The wireless transmitter 160, along with the antenna 170, (5) transmits the signal wirelessly (6) to the receiver 200, which is positioned remote of the wireless camera 100. The receiver 200 then feeds the signal (7) to the video monitor 300 to display the signal as a video image.

Figure 4:
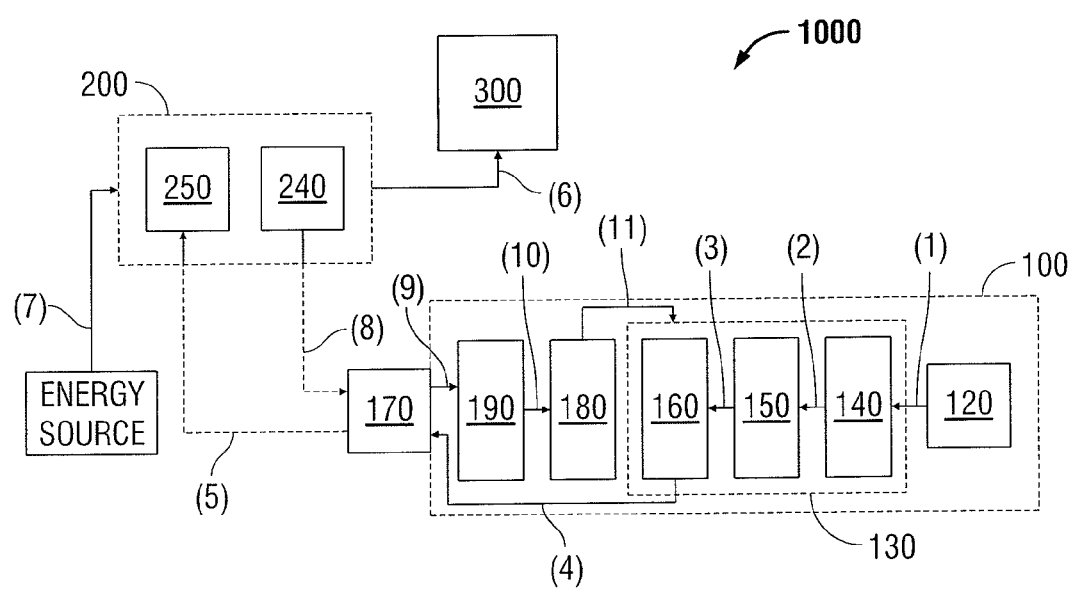
FIG. 4 is a block diagram of the laparoscopic camera system of FIG. 1.

With continued reference to FIG. 4, the wireless receiver 200 may be configured as a transceiver including a transmitting component 240, for wirelessly transferring power to the battery charging circuit 190, and a receiving component 250, for receiving the signal from the wireless transmitter 160. More particularly, the transceiver 200, which is coupled (8) to an energy source, transmits (9) energy, e.g., radio frequency (RF) energy, to the battery charging circuit 190 (10). The battery charging circuit 190 converts the RF energy into power to charge (11) the batteries 180, which, in turn power (12) the chip package 130.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A wireless laparoscopic camera system, comprising:
   a housing defining a longitudinal axis and having a proximal end and a distal end, the housing configured for insertion into an internal body cavity;
   a lens disposed at the distal end of the housing and radially-centered about the longitudinal axis of the housing; and a chip package disposed within the housing and positioned proximal of the lens, the chip package including an image sensor, a processing component, and a wireless transmitter, each of the image sensor, the processing component, and the wireless transmitter radially-centered about the longitudinal axis of the housing, the image sensor, processing component, and wireless transmitter configured as bare die stacked and coupled in sequence with respect to one another to form the chip package, wherein the chip package is configured to convert an optical image produced by the lens into a signal and to wirelessly transmit the signal to a wireless receiver positioned remote of the housing.

2. The wireless laparoscopic camera system according to claim 1, further comprising an antenna disposed at the proximal end of the housing, the antenna configured to facilitate transmission of the signal to the wireless receiver.

3. The wireless laparoscopic camera system according to claim 1, wherein the wireless receiver is coupled to a video display for displaying the transmitted signal as a video image.

4. The wireless laparoscopic camera system according to claim 1, further comprising at least one battery disposed within the housing, the at least one battery configured to provide power to the chip package.

5. The wireless laparoscopic camera system according to claim 4, further comprising a battery charging circuit disposed within the housing and coupled to the at least one battery, the battery charging circuit configured to charge the at least one battery.

6. The laparoscopic camera system according to claim 5, further comprising a power transmitter positioned remote of the housing, the power transmitter configured to wirelessly transmit power to the battery charging circuit.

7. The laparoscopic camera system according to claim 6, wherein the power transmitter wirelessly transmits power to the battery charging circuit by radio frequency (RF) power transfer.

8. The laparoscopic camera system according to claim 1, wherein the housing includes a clip disposed on an outer surface thereof, the clip configured to releasably engage the housing to a surgical instrument.

9. A surgical system, comprising:
   a surgical instrument including an end effector assembly disposed at a distal end thereof, the end effector assembly insertable into and configured to perform at least one surgical task within an internal surgical site; and
   a camera system releasably engagable with the surgical instrument and located near the distal end thereof, the camera system insertable into the internal surgical site with the end effector assembly and configured to provide visualization of the internal surgical site during the at least one surgical task, the camera system including:
      a housing defining a longitudinal axis and having a proximal end and a distal end;
      a lens disposed at the distal end of the housing and radially-centered about the longitudinal axis of the housing; and
      a chip package disposed within the housing and positioned proximal of the lens, the chip package including an image sensor, a processing component, and a wireless transmitter, each of the image sensor, the processing component, and the wireless transmitter radially-centered about the longitudinal axis of the housing, the image sensor, processing component, and wireless transmitter configured as bare die stacked and coupled in sequence with respect to one another to form the chip package, wherein the chip package is configured to convert an optical image produced by the lens into a signal and to wirelessly transmit the signal to a wireless receiver positioned remote of the housing.

10. The system according to claim 9, wherein the camera system further comprises an antenna disposed at the proximal end of the housing, the antenna configured to facilitate transmission of the signal to the wireless receiver.

11. The system according to claim 9, wherein the wireless receiver is coupled to a video display for displaying the transmitted signal as a video image.

12. The system according to claim 9, wherein the camera system further comprises at least one battery disposed within the housing, the at least one battery configured to provide power to the chip package.

13. The system according to claim 9, further comprising a clip configured to releasably engage the camera system to the surgical instrument.

14. The system according to claim 9, wherein the surgical instrument includes a housing and a shaft extending distally from the housing, wherein the end effector assembly is disposed at a distal end of the shaft, and wherein the camera system is releasably engaged to the shaft of the surgical instrument.

* * * * *